United States Patent [19]
Dorwald

[11] Patent Number: 5,847,150
[45] Date of Patent: Dec. 8, 1998

[54] SOLID PHASE AND COMBINATORIAL SYNTHESIS OF SUBSTITUTED 2-METHYLENE-2, 3-DIHYDROTHIAZOLES AND OF ARRAYS OF SUBSTITUTED 2-METHYLENE-2, 3-DIHYDROTHIAZOLES

[75] Inventor: Florencio Zaragoza Dorwald, Herlev, Denmark

[73] Assignee: Novo Nordisk A/S, Bagsvaerd, Denmark

[21] Appl. No.: 842,629

[22] Filed: Apr. 16, 1997

[30] Foreign Application Priority Data

Apr. 24, 1996 [DK] Denmark ................................. 488/96

[51] Int. Cl.$^6$ .................................................. C07D 277/14
[52] U.S. Cl. ........................... 548/146; 548/187; 544/367
[58] Field of Search ..................... 548/146, 187; 544/367

[56] References Cited

PUBLICATIONS

Neplyuev et al., Institute of Organic Chemistry, vol. 9, pp. 1186–1187 (Sep., 1971).
Laliberte et al., Canadian Journal of Chemistry, vol. 48, pp. 2709–2717 (1970).
F. Zaragoza, Tetrahedron Letters, vol. 36, No. 47, pp. 8677–8678 (1995).
E.R. Felder, Chimia, vol. 48, pp. 531–541, (1994).
E.M. Gordon, Current Biology Ltd., vol. 6, pp. 624–631 (1995).
Fruchtel et al., Angew Chem. Int. Ed., vol. 35, pp. 17–42, (1996).

*Primary Examiner*—Johann Richter
*Assistant Examiner*—Laura R. C. Lutz
*Attorney, Agent, or Firm*—Steve T. Zelson; Elias J. Lambiris

[57] ABSTRACT

A solid phase method for the synthesis of a plurality of differently substituted 2-methylenethiazoles with a wide variety of side-chain substituents as compounds of potential therapeutic interest. The 2-methylenethiazoles are prepared by acylation of a substrate-bound primary or secondary amine with cyanoacetic acid and reaction of the resulting cyanoacetamide with an isothiocyanate in the presence of a base. Alkylation with an appropriate alkyl halide under acidic conditions yields differently substituted, support-bound 2-methylene-2,3-dihydrothiazoles. These may be screened on the substrate or cleaved from the substrate and then screened in solution. The efficient synthesis of a wide variety of 2-methylenethiazoles using automated synthesis technology of the present method makes these compounds attractive candidates for the generation and rapid screening of diverse thiazole-based libraries. The method disclosed here provides an easy and fast access to highly diverse heterocyclic compounds of therapeutic interest, amenable to automatization.

2 Claims, No Drawings

SOLID PHASE AND COMBINATORIAL SYNTHESIS OF SUBSTITUTED 2-METHYLENE-2, 3-DIHYDROTHIAZOLES AND OF ARRAYS OF SUBSTITUTED 2-METHYLENE-2, 3-DIHYDROTHIAZOLES

CROSS-REFERENCE TO RELATED APPLICATIONS

This application claims priority under 35 U.S.C. 119 of Danish application 488/96 filed Apr. 24, 1996, the contents of which are fully incorporated herein by reference.

BACKGROUND OF THE INVENTION

The present invention relates to the field of solid phase chemistry. More specifically, the invention provides a method for solid phase and combinatorial synthesis of organic compounds, and most particularly, a therapeutically important class of compounds, namely diversely substituted 2-methylene-2,3-dihydrothiazoles, in the following called 2-methylenethiazoles or thiazoles.

Obtaining a better understanding of the important factors in molecular recognition in conjunction with developing new therapeutic agents is a major focus of scientific research. Methods have recently been developed, which permit the fast generation of large arrays of pure compounds or of mixtures of compounds, which are then screened against a specific receptor or enzyme. However, there are still only few methods available for the fast synthesis of organic compounds other than peptides or oligonucleotides. The latter tend to have very short clearing times, so that their utility as bioavailable therapeutic agent will be limited. For this reason, organic compounds of potential therapeutic interest are today still synthesized and evaluated one at a time, thus dramatically limiting the number of derivatives which can be screened. It is therefore of utmost importance to develop new synthetic methodology, which permits the fast synthesis of bioavailable organic compounds of potential therapeutic interest, such as small heterocyclic compounds. This may be achievable by developing a solid phase synthesis for such compounds, since experience has shown, that solid phase synthesis is amenable to automatization and can yield products of high purity without the need of any tedious and time consuming purification steps.

The realization of known synthetic reactions on a solid support may not always be possible and may require careful optimization of the reaction conditions. Although solid phase synthesis, once implemented and optimized, offers many advantages if compared to syntheses in liquid phase, the finding of the appropriate reaction conditions may be a difficult task. This may be due to the limited choice of solvents which may be used with some types of supports, as well as the difficulty of precise temperature adjustment in arrays of reactors for solid phase synthesis. Additionally, the classical tools for the quality control of intermediates (infrared spectroscopy, nuclear magnetic resonance spectroscopy, mass spectrometry) may only be of limited use in solid phase synthesis. For these reasons, the implementation of known reactions to a solid support may often require a major effort and time investment.

The synthetic sequence disclosed in this invention is a variant of related 2-methylenethiazole syntheses (ref. 11–16), adapted and optimized for its realization on a solid support.

Terminology

The following terms are intended to have the following, general meanings:

1. Substrate: refers to any insoluble or partially insoluble material, to which compounds may be covalently attached. Substrates may be selected from the group consisting of any kind of organic or inorganic polymeric or oligomeric compound, e.g. polystyrene with different grades of crosslinking, polyethylene glycol (PEG), polyethylene glycol attached to polystyrene (e.g. TentaGel), polyacrylamides, polyacrylates, polyurethanes, polycarbonates, polyamides, polysaccharides or silicates.

2. Linker: a molecule with at least two reactive sites, which permit its covalent attachment to other molecules or to a substrate. Either the bond of the linker to the substrate or the bond of the linker to other molecules attached to it or the linker itself must be cleavable upon selective exposure to an activator such as a selected chemical activator or other specific conditions, e.g. by treatment with a strong acid or by exposure to electromagnetic radiation or by metal catalysis.

3. Array: A collection of N single compounds or N mixtures of compounds with a common structural element, synthesized simultaneously in a parallel fashion using the same synthetic reaction sequence. The precise structure of a single compound within an array of compounds or the components of a mixture within an array of mixtures is determined by the sequence of reactants which gave rise to this compound or mixture and can be deduced from the recorded reaction-protocol. The spatial arrangement of the array is irrelevant.

4. Thiazole: Five-membered heterocyclic compound containing one nitrogen atom and one sulphur atom in the five-membered ring.

5. Protecting group: A material which is chemically bound to a molecule or a substrate and which may be removed upon selective exposure to an activator such as a selected chemical activator or other specific conditions, e.g. by treatment with a strong acid or by exposure to electromagnetic radiation or by metal catalysis.

6. Combinatorial synthesis: an ordered strategy for parallel synthesis of arrays of single compounds or mixtures, by sequential addition of reagents.

7. Receptor: A material that has an affinity for a given ligand. Receptors may be naturally-occurring or synthetic molecules or aggregates of molecules. Also, they can be employed in their unaltered state or as aggregates with other species. Receptors may be attached, covalently or non-covalently, to a binding material or a substrate, either directly or via a linking substance. Examples of receptors which can be employed by this invention include, but are not restricted to, antibodies, monoclonal antibodies and antisera reactive with specific antigenic determinants (such as viruses, cells or other materials), cell membrane receptors, drugs, oligonucleotides, polynucleotides, nucleic acids, peptides, cofactors, small organic molecules, lectins, sugars, oligosaccharides, cells, cellular membranes, organelles, microorganism receptors, enzymes, catalytic polypeptides, hormone receptors, primary metabolite receptors such as carbohydrate receptors, nucleotide receptors or lipid receptors and secondary metabolite receptors such as opiate receptors, prostaglandine receptors, etc.

8. Electrophile: A material capable of reacting under bond-formation with electron-rich sites of a molecule 9. Abbreviations: The following frequently used abbreviations are intended to have the following meanings:

AcOH: glacial acetic acid
DCM: dichloromethane, methylenechloride
DMF: N,N-dimethyl formamide
FMoc: fluorenylmethyloxycarbonyl
R: organic radical TFA: trifluoroacetic acid
THF: tetrahydrofurane

SUMMARY OF THE INVENTION

An improved method for the synthesis of therapeutically useful compounds is provided by virtue of the present invention. The invention provides a rapid approach for combinatorial synthesis and screening of arrays of 2-methylenethiazole derivatives as a therapeutically important class of compounds. It provides a solid phase synthesis of these derivatives, which eliminates purification and isolation steps and thus highly increases synthesis efficiency. This patent disclosure also describes an important extension of solid phase synthesis methods to nonoligomeric organic compounds.

A further understanding of the nature and advantages of the invention may be realized by reference to the remaining portions of the specification.

DESCRIPTION

The application of the present invention is the rapid preparation and screening, preferably in parallel and simultaneous fashion, of a large number of differently substituted 2-methylenethiazoles of the general formula Ia or Ib

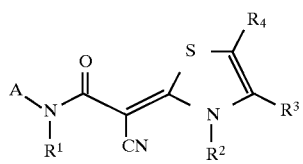

Ia and

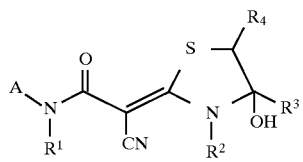

Ib wherein

A is a hydrogen atom or a group of formula

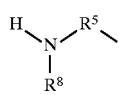

or

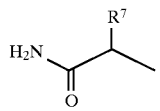

wherein $R^5$ is alkylene optionally substituted with hydrogen, alkyl, aryl, heteroaryl, alkoxy, aryloxy, cyano, hydroxy, dialkylamino, arylalkylamino, diarylamino or halogen;

$R^6$ is hydrogen, alkyl optionally substituted with hydroxy, halogen, cyano, alkoxy, aryloxy, dialkylamino, arylalkylamino or diarylamino; or aralkyl;

$R^5$ and $R^6$ may be covalently linked to each other by a covalent bond or an additional alkylene group $R^5$, preferentially giving rise to a fragment of the type shown below

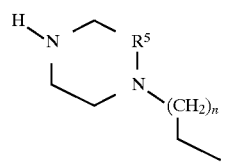

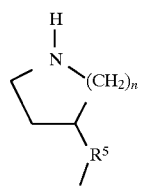

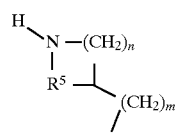

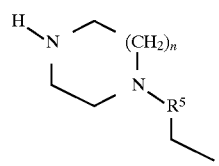

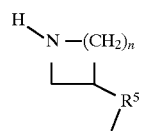

wherein n and m are integers between 0 and 15, preferentially 0 and 3;

$R^7$ is hydrogen, alkyl, alkyl substituted with hydroxy, alkoxy, aryloxy, alkylthio, arylthio, dialkylamino, arylalkylamino or diarylamino; aralkyl, aryl, aryl substituted with alkyl, aryl, heteroaryl, halogen, alkoxy, aryloxy, dialkylamino, alkylarylamino, diarylamino, halogen, cyano, alkoxycarbonyl or aminocarbonyl;

$R^1$ is hydrogen, alkyl optionally substituted with hydroxy, halogen, cyano, alkoxy, aryloxy, dialkylamino, arylalkylamino or diarylamino; or aralkyl;

$R^1$ may be covalently linked to A, $R^5$, $R^6$ and/or $R^7$, in which case —$R^1$—A— or —$R^1$—$R^5$— represents low alkylene, preferentially methylene, ethylene or propylene, unsubstituted or substituted with alkyl, hydroxy, alkoxycarbonyl, alkoxy or dialkylamino, —$R^1$—$R^6$— represents ethylene or propylene, unsubstituted or substituted with alkyl, hydroxy, alkoxy or dialkylamino, and/or —$R^1$—$R^7$— represents methylene, propylene or butylene unsubstituted or substituted with alkyl, hydroxy, alkoxycarbonyl, alkoxy or dialkylamino;

$R^2$ is alkyl optionally substituted with aryl, heteroaryl, alkoxy, aryloxy, cyano, dialkylamino, arylalkylamino, diarylamino or halogen;

aryl optionally substituted with alkyl, aryl, heteroaryl, halogen, alkoxy, aryloxy, dialkylamino, alkylarylamino, diarylamino, halogen, cyano, alkoxycarbonyl or aminocarbonyl;

heteroaryl optionally substituted with alkyl, aryl, heteroaryl, halogen, alkoxy, aryloxy, dialkylamino, alkylarylamino, diarylamino, halogen, cyano, alkoxycarbonyl or aminocarbonyl; and $R^3$ is cyano, alkyl optionally substituted with alkoxycarbonyl or halogen, aryl optionally substituted with alkyl, aryl, heteroaryl, halogen, alkoxy, aryloxy, dialkylamino, alkylarylamino, diarylamino, halogen, cyano, alkoxycarbonyl or aminocarbonyl, heteroaryl or alkoxycarbonyl;

R$^4$ is hydrogen or substituted or unsubstituted alkyl, acyl, aminocarbonyl or aryl;

and pharmaceutically acceptable salts thereof;

or of the general formula IIa or IIb

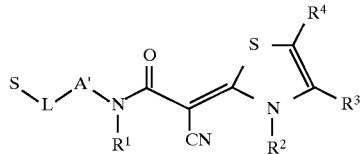

IIa and

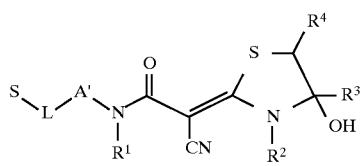

IIb wherein S is a substrate,

L is a chemical bond or a linker,

A' is a chemical bond or a group of formula

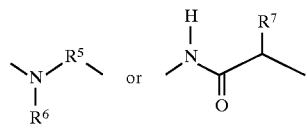

wherein

R$^5$ is alkylene optionally substituted with hydrogen, alkyl, aryl, heteroaryl, alkoxy, aryloxy, cyano, hydroxy, dialkylamino, arylalkylamino, diarylamino or halogen;

R$^6$ is hydrogen, alkyl optionally substituted with hydroxy, halogen, cyano, alkoxy, aryloxy, dialkylamino, arylalkylamino or diarylamino; or aralkyl;

R$^5$ and R$^6$ may be covalently linked to each other by a covalent bond or an additional alkylene group R$^5$, preferentially giving rise to a fragment of the type shown below

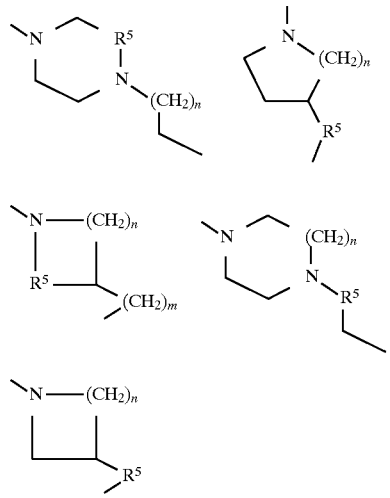

wherein n and m are integers between 0 and 15, preferentially 0 and 3;

R$^7$ is hydrogen, alkyl, alkyl substituted with hydroxy, alkoxy, aryloxy, alkylthio, arylthio, dialkylamino, arylalkylamino or diarylamino; aralkyl, aryl, aryl substituted with alkyl, aryl, heteroaryl, halogen, alkoxy, aryloxy, dialkylamino, alkylarylamino, diarylamino, halogen, cyano, alkoxycarbonyl or aminocarbonyl;

R$^1$ is hydrogen, alkyl optionally substituted with hydroxy, halogen, cyano, alkoxy, aryloxy, dialkylamino, arylalkylamino or diarylamino; or aralkyl;

R$^1$ may be covalently linked to A, R$^5$, R$^6$ and/or R$^7$, in which case —R$^1$—A— or —R$^1$—R$^5$— represents low alkylene, preferentially methylene, ethylene or propylene, unsubstituted or substituted with alkyl, hydroxy, alkoxycarbonyl, alkoxy or dialkylamino, —R$^1$—R$^6$— represents ethylene or propylene, unsubstituted or substituted with alkyl, hydroxy, alkoxy or dialkylamino, and/or —R$^1$—R$^7$— represents methylene, propylene or butylene unsubstituted or substituted with alkyl, hydroxy, alkoxycarbonyl, alkoxy or dialkylamino;

R$^2$ is alkyl optionally substituted with aryl, heteroaryl, alkoxy, aryloxy, cyano, hydroxy, dialkylamino, arylalkylamino, diarylamino or halogen;

aryl optionally substituted with alkyl, aryl, heteroaryl, halogen, alkoxy, aryloxy, dialkylamino, alkylarylamino, diarylamino, halogen, cyano, alkoxycarbonyl or aminocarbonyl;

heteroaryl optionally substituted with alkyl, aryl, heteroaryl, halogen, alkoxy, aryloxy, dialkylamino, alkylarylamino, diarylamino, halogen, cyano, alkoxycarbonyl or aminocarbonyl; and R$^3$ is cyano, alkyl optionally substituted with alkoxycarbonyl or halogen, aryl optionally substituted with alkyl, aryl, heteroaryl, halogen, alkoxy, aryloxy, dialkylamino, alkylarylamino, diarylamino, halogen, cyano, alkoxycarbonyl or aminocarbonyl, heteroaryl or alkoxycarbonyl;

R$^4$ is hydrogen or substituted or unsubstituted alkyl, acyl, aminocarbonyl or aryl;

and pharmaceutically acceptable salts thereof.

Presently in drug development, high throughput screening is playing a key role. High throughput screening generally incorporates automation and robotics, thus making it possible to screen thousands of compounds in one or more bioassays in a short period of time. This technique has created the need for an automated production of large numbers of different compounds for being screened. A robotic, fully automated system for the production and screening of highly diverse compounds as potential lead-candidates will dramatically speed up the discovery and optimization of new leads for all types of human diseases.

Traditionally, new compounds for lead-discovery or structural analogues for lead-optimization have been synthesized by multiple step linear syntheses. Linear syntheses involve the sequential reactions of several separate reactants in order to obtain the final product. Linear syntheses require the isolation, purification and characterization by spectroscopic and other analytical tools of the intermediate reaction products. Such a linear synthesis is therefore a very time consuming process, which requires a high skill in the synthetic organic chemical art. Since this traditional way of producing compounds is too inefficient for fully exploiting the screening-potential of presently available systems for high throughput screening, synthetic methodology is required, which permits the automated synthesis of large numbers of different compounds.

Parallel solid phase synthesis is today one of the fastest ways of producing arrays of single compounds or arrays of defined mixtures of compounds. However, there are still only few methods available for the parallel solid phase synthesis of organic compounds other than peptides or oligonucleotides. A principal disadvantage associated with peptidic or other bio-oligomeric leads is their low metabolic stability, due to in vivo proteolysis. For this reason, other type of compounds with a higher metabolic stability would be more attractive as leads. Of special interest in this context are small heterocyclic and heteroaromatic compounds, which have been proven to be very useful in many applications. Also as drugs for the treatment of different human metabolic disorders, small heterocyclic compounds have played and are playing a decisive role. For this reason, the solid phase synthesis of heterocyclic compounds is a highly demanded technology, which will be extremely valuable for the fast production of large numbers of potential leads for high volume throughput screening.

Thiazoles are important core structures for biologically active compounds (see e.g. ref 17).

Thiazoles have been used for instance as anti-inflammatories (lotifazole, sudoxicam, fentiazac, myalex), anticonvulsants (chlomethiazole), antiparasitics (nitridazole), antibacterials (ceftriaxone, ceftizoxime, ceftioxide, ceftiolene, ceftiofur, cefteram, cefuzonam, nifurthiazole, sulfasomizole, nitrosulfathiazole), antihistaminics (famotidine, nizatidine), immunoregulators (enoxamast, frentizole), antifungals (diamthazole, etisazole, fezatione), dopaminergics (etrabamine), diuretics (ethoxzolamide, etozolin), antidiabetics (epalrestat) and narcotic antagonists (amiphenazole).

Many more thiazoles than those described so far may be postulated, however, to be potential drug candidates. To achieve the preparation and screening of a large number of compounds with 2-methylenethiazole-core-structure, the present invention provides a solid phase synthesis for 2-methylene-2,3-dihydrothiazoles in which variable substituent groups are independently attached to a common central thiazole ring. The generally recognized advantages of solid phase synthesis are the absence of purification steps of intermediates or the final product, as well as the possibility of automation. Due to these features, a solid phase synthesis of 2-methylenethiazoles dramatically increases the synthesis efficiency for these therapeutically important compounds.

An overall illustration of the solid phase synthesis of 2-methylenethiazoles is shown in reaction Scheme 1.

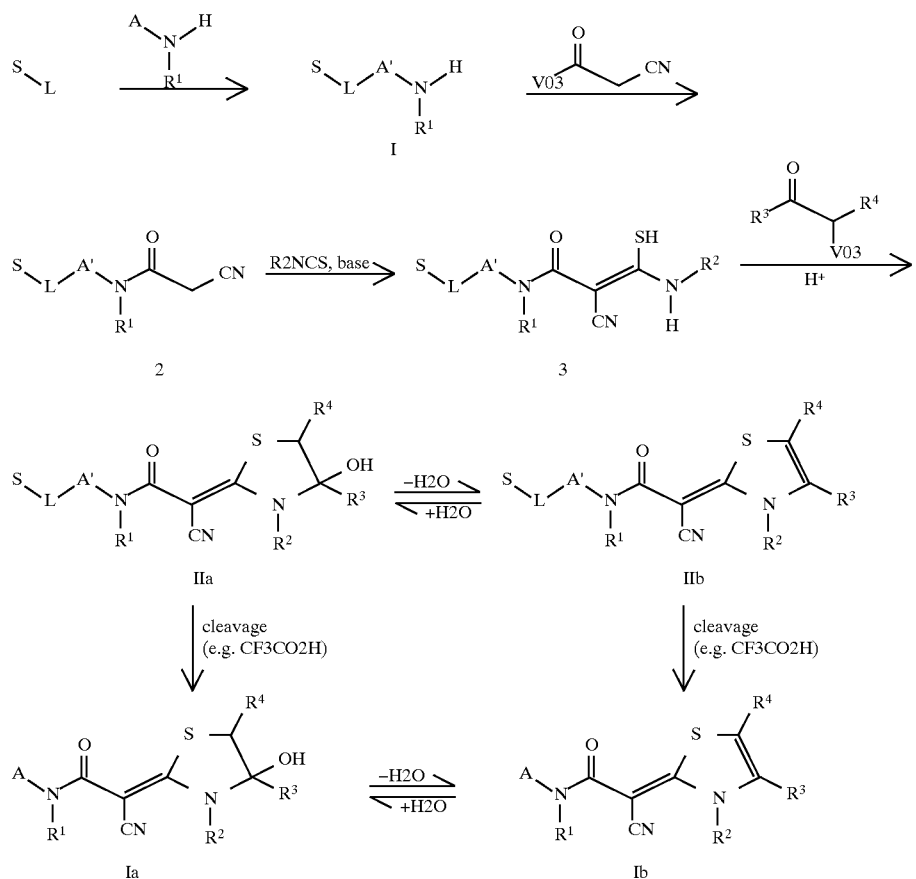

Scheme 1

In the following description of this invention, R is intended to be an organic radical. Alkyl is intended to mean lower straight, cyclic, fused or branched alkyl having 1 to 15 carbon atoms, preferentially 1 to 6 carbon atoms. Aryl is intended to mean phenyl optionally substituted with alkyl or phenyl, or optionally fused with cycloalkyl, or polycyclic aromatic systems such as naphthyl, anthracenyl, phenanthrenyl, fluorenyl, etc. Alkylene is intended to mean lower straight, cyclic, fused or branched alkylene having 1 to 15 carbon atoms, preferentially 1 to 6 carbon atoms. Heteroaryl is intended to mean any of the possible isomeric, unsubstituted or alkyl-substituted pyrrolyl, furyl, thienyl, imidazolyl, pyrazolyl, triazolyl, tetrazolyl, oxazolyl, thiazolyl, oxadiazolyl, thiadiazolyl, pyridyl, pyrazinyl, pyrimidinyl and pyridazinyl, as well as the corresponding benzo and dibenzo derivatives or other fused ring-systems thereof. Heteroaryl is also intended to mean the partially or fully hydrogenated derivatives of the heterocyclic systems enumerated above. Alkoxy is intended to mean —O-alkyl and aryloxy is intended to mean —O-aryl. Cyano is intended to mean —CN, hydroxy is intended to mean —OH, amino is intended to mean —$NH_2$ and nitro is intended to mean —$NO_2$. Dialkylamino is intended to mean —$N(alkyl)_2$. Alkylarylamino is intended to mean —N(alkyl)(aryl) and diarylamino is intended to mean —$N(aryl)_2$. Halogen is intended to mean —F, —Cl, —Br and —I. Aralkyl is intended to mean —alkylene-aryl. Alkylthio is intended to mean —S-alkyl and arylthio is intended to mean —S-aryl. Alkoxycarbonyl is intended to mean —CO—O— alkyl and aminocarbonyl is intended to mean —CO—$N(alkyl)_2$, —CO—N(alkyl)(aryl) or —CO—$N(alkyl)_2$. Acylamino is intended to mean —N(alkyl)—CO-alkyl or —N(alkyl)-CO-aryl. A leaving group is intended to be a group or atom capable of existing in solution as a negatively charged species, or a positively charged group or atom.

In this synthesis, an organic molecule of the form $HN(R^6)$—$R^5$—$N(R^1)H$ or $HO_2C$—$CH(R^7)$—$N(R^1)P$, P being a protecting group, is attached to a substrate by well precedented methods, optionally followed by a deprotection step, in such a way, that a free primary or secondary amino group is generated on the support.

The substrate may be any insoluble or partially insoluble material, to which compounds may be covalently attached. Preferentially, the substrates may be selected from the group consisting of polystyrene, polyethylene glycol (PEG), polyethylene glycol attached to polystyrene (e.g. TentaGel), polyamides, polysaccharides and silicates. Depending on the type of substrate chosen, different types of solvents or protecting groups may be used.

Most preferentially, in the case of diamines attached to a substrate, a polystyrene resin or TentaGel resin, covalently attached to a Wang linker (Wang, S. *J. Am. Chem. Soc.* 1973, 95, 1328–1333), may first be treated with phosgene or a phosgene equivalent, such as 4-nitrophenyl chloroformate or carbonyldiimidazole in a suitable solvent such as DCM, THF, toluene, DMF or mixtures thereof, optionally in the presence of a base, such as pyridine, and then with an excess of a diamine such as ethylenediamine, N,N'-dimethylethylenediamine, N,N'-diethylethylenediamine, N,N'-dipropylethylenediamine, N,N'-diisopropylethylenediamine, N,N'-di-butylethylenediamine, N,N'-dihexylethylenediamine, N,N'-dibenzylethylenediamine, N,N'-di(1-hydroxymethyl) propylethylenediamine, piperazine, 2-methylpiperazine, 2,6-dimethylpiperazine, 2,5-dimethylpiperazine, 1,4-diazacycloheptane, 6-hydroxy-1,4-diazacycloheptane, 6-acetoxy-1,4-diazacycloheptane, 1,2-diaminopropane, 1,3-diaminopropane, 1,3-diamino-2-propanol, N,N'-dimethyl-1,3-propanediamine, N,N'-diethyl-1,3-propanediamine, 2,2-dimethyl-1,3-propanediamine, N,N',2-tri-methyl-1,3-propanediamine, 1,4-diaminobutane, N,N'-dipropyl-1,4-butanediamine, N,N'-diethylbutane-1,4-diamine, N,N'-dimethyl-2-butene-1,4-diamine, N,N'-diethyl-2-butene-1,4-diamine, N,N'-diethyl-2-butyne-1,4-diamine, 1,5-diaminopentane, 1,3-diaminopentane, 1,2-diaminocyclohexane, 1,3-diaminocyclohexane, 1,4-diamino-cyclohexane, 1,3-bis(aminomethyl)cyclohexane, 1,4-bis(aminomethyl)cyclohexane, 4,4'-bipiperidine, 1-[2-(3-pyridylmethylamino)ethyl]-piperazine, 1-(2-aminoethyl) piperazine, 4-aminomethylpiperidine, 3-(4-aminobutyl) piperidine, 5-amino-2,2,4-trimethyl-1-cyclopentanemethylamine, 4,4'-diaminodicyclohexylmethane, o-xylylenediamine, m-xylylenediamine, p-xylylenediamine or isophoronediamine to give a substrate-bound diamine of the general formula [polystyrene]-[Wang linker]—O—CO—$N(R^6)$—$R^5$—$N(R^1)H$. The preparation of such substrate-bound diamines has occasionally been described in literature (e.g. Hiroshige, M.; Hauske, J. R.; Zhou, P. *J. Am. Chem. Soc.* 1995, 117, 11590–11591; Zaragoza, F. *Tetrahedron Lett.* 1995, 36, 8677–8678; Dixit, D. M.; Leznoff, C. C. Israel *J. Chem.* 1978, 17, 248–252; Dixit, D. M.; Leznoff, C. C. *J. Chem. Soc., Chem. Commun.* 1977, 798–799; Kaljuste, K.; Unden, A. *Tetrahedron Lett.* 1995, 36, 9211–9214).

In the case of protected amino acids attached to a substrate, a polystyrene resin or TentaGel, covalently attached to a Rink linker (H. Rink, *Tetrahedron Lett.* 1987, 28, 3787), may be acylated with a derivative of a side-chain and nitrogen-protected (e.g. FMoc) amino acid, such as FMoc-glycine, FMoc-phenylglycine, FMoc-sarcosine, FMoc-alanine, FMoc-valine, FMoc-norvaline, FMoc-leucine, FMoc-isoleucine, FMoc-norleucine, FMoc-penicillamine, FMoc-arginine, FMoc-asparagine, FMoc-aspartic acid, FMoc-citrulline, FMoc-glutamine, FMoc-glutamic acid, FMoc-proline, FMoc-hydroxyproline, FMoc-phenylalanine, FMoc-tyrosine, FMoc-tryptophan, FMoc-threonine, FMoc-histidine, FMoc-serine, FMoc-cysteine, FMoc-methionine, FMoc-lysine, FMoc-statine or FMoc-ornithine, by well established procedures, for example with the in situ generated symmetric anhydride of these amino acid derivatives. Most of the FMoc-amino acids and some of the resulting substrate-bound FMoc-amino acids are commercially available. After this acylation step, the nitrogen protecting group may be removed by well established methods, such as treatment with piperidine in DMF in the case of an FMoc-protecting group, to give a substrate-bound amino acid of the general formula [polystyrene or Tentagel]—[Rink linker]—NH—CO—$C(R^7)H$—$N(R^1)H$. Also non-natural amino acid derivatives may be attached to a substrate-bound Rink linker and converted, by an optional deprotection step, into support-bound amino acids of the type 1 (scheme 1).

The substrate-bound primary or secondary amine 1 may then be acylated with an appropriate cyanoacetic acid derivative of the general structure NC—$CH_2$—COX, X being a leaving group, preferentially with the in situ generated symmetric anhydride (Zaragoza, F. *Tetrahedron Lett.* 1995, 36, 8677–8678). Alternatively, other, in situ generated or isolated derivatives of cyanoacetic acid may be used as acylating reagents, such as the mixed anhydrides derived from alkyl chloroformates and cyanoacetic acid, or the imidazolide or other types of activated esters, such as the N-hydroxybenzotriazolyl ester or N-hydroxysuccinyl ester or other activated esters, obvious to those skilled in the art.

Alternatively, a cyanoacetic acid derivative may be directly reacted with a Ring linker attached to a substrate, to give a derivative of the general formula [substrate]—[Rink linker]—NH—CO—$CH_2$—CN. This corresponds to the case, where A' (scheme 1) is a chemical bond and A is hydrogen.

The resulting, resin bound cyanoacetamide 2 may then be treated with an excess of an aromatic or aliphatic isothiocyanate of the general structure $R^2$—NCS in an appropriate solvent such as DMF or THF, in the presence of a base, preferentially 1,8-diazabicyclo[5.4.0]undec-7-ene (DBU).

The group $R^2$ may be straight or branched alkyl groups, such as methyl, ethyl, propyl, isopropyl, butyl, including n-butyl, sec-butyl, iso-butyl, tert-butyl, pentyl, hexyl, heptyl, octyl, etc., and their variants, straight or branched alkylene chains such as methylene, 1,2-ethylene, 1,1-ethylene, propylene, etc. linked to cycloalkyl groups, substituted or unsubstituted aryl groups such as phenyl, naphthyl, biphenylyl or monovalent radicals of substituted or unsubstituted heterocycles and heteroaromatics such as pyridyl, thienyl, pyrrolyl, furyl, piperidinyl, pyrrolidinyl, etc. Additionally, $R^2$ may be substituted or unsubstituted aryl groups or substituted or unsubstituted heterocycles or heteroaromatics. All these groups may also be substituted with functional groups such as F, Cl, Br, I, $CONR_2$, $CO_2R$, CN, $NO_2$, SR, SOR, $SO_2R$, $SO_2NR_2$, OR or $NR_2$, R being low alkyl or aryl.

The resulting intermediate product 3 may then be alkylated at the sulphur atom with an alkylating agent of the general structure $R^3CO$—$CHR^4$—X, X being a leaving group for nucleophilic displacement and $R^3$ and $R^4$ being independently substituted or unsubstituted alkyl or aryl groups, in an appropriate solvent such as DMF, DCM, THF, acetonitrile or alcohols, under acidic conditions. This alkylation may give rise to a support-bound thiazole of the type II, which, depending on the nature of the substituents $R^2$, $R^3$ and $R^4$ may either remain hydrated (formula IIa) or dehydrate (formula IIb) under the acidic reaction conditions. The choice of solvent and acid may depend on the type of substrate used.

Cleaving of the linker of the product IIa or IIb may release the thiazole derivative Ia or Ib into solution. Cleavage conditions will depend upon the type of substrate and linker chosen. E.g., in the case of a polystyrene resin with a Wang linker or a Rink amide linker treatment of the support-bound thiazole IIa or IIb with TFA may lead to a cleavage of the linker.

Again, the nature of the substituents $R^2$, $R^3$ and $R^4$ may determine, if the thiazoles remain hydrated or elimination of water occurs under the acidic cleavage conditions. Electron-rich substituents, especially an electron-rich substituent $R^3$ may facilitate water elimination. On the other hand, strongly electron withdrawing substituents, especially an electron withdrawing substituent $R^3$ may inhibit the elimination of water.

Using this synthetic method, arrays of thiazole derivatives may be constructed with the help of a device for parallel solid phase synthesis. This may be either the pin method developed by Geysen et al. (*J. Immunol. Meth.* 1987, 102, 259–274) or a device with several reactors for solid phase synthesis (containers with a permeable wall), which permits the automated addition of reagents and solvents, as well as the removal of the solvents from the reactors by simultaneous or individual application of a pressure difference between the inside and the outside of the permeable wall of the reactors.

Such an array may be prepared on a multiple organic synthesizer (e.g. "ACT 496" of "Advanced ChemTech") by individually reacting under the conditions specified below different amines attached to a substrate and located in individual containers, first with a derivative of cyanoacetic acid of the general formula NC—$CH_2$—COX, X being a suitable leaving group, and then with different isothiocyanates of the general formula $R^2$—NCS in the presence of a base. The resulting intermediates 3 may then be reacted individually with different alkylating agents of the general structure $R^3CO$—$CHR^4$—X, X being a leaving group for nucleophilic displacement, under acidic conditions to give, after optional cleavage from the support, an array of different 2-methylenethiazole derivatives Ia or Ib, or IIa or IIb.

The present invention also permits the synthesis of arrays of mixtures of 2-methylenethiazole derivatives. This can be achieved either by the "split and mix" method (Sepetov, N. F., Krchnak, V., Stankova, M., Wade, S., Lam, K. S., and Lebl *Proc. Natl. Acad. Sci. USA* 1995, 92, 5426–5430) or by using mixtures of the corresponding reagents.

By virtue of the present invention basically two different types of arrays of thiazoles Ia, Ib or IIa, IIb may be constructed: fully combinatorial arrays (FCA) and not-fully combinatorial arrays (NFCA).

By FCA we refer to arrays of substituted thiazoles, in which all the possible combinations of a set of selected building blocks (R-groups) are realized. As an example, a FCA of N thiazoles may be prepared by selecting n diamines, m isothiocyanates and p haloketones so that n×m×p=N, and synthesizing all the N possible combinations of diamine/isothiocyanate/haloketone. The selection of building blocks may be done with regard to the expected properties of the members of the array.

By NFCA we refer to arrays of substituted thiazoles, in which only a selection of the possible combinations of a set of selected building blocks is realized. As an example, a NFCA of N thiazoles may be prepared by first selecting n diamines, m isothiocyanates and p haloketones so that n×m×p>N. Then a selection of N thiazoles from all the n×m×p theoretically possible thiazoles is done by grouping all the n×m×p possible thiazoles into N groups of thiazoles with similar expected properties and selecting from each of these groups one thiazole, which is then synthesized. The selection of building blocks and of thiazoles may be done with regard to the expected properties of the members of the array.

For the preparation of such arrays of compounds, the exact positions of the substrate does, by itself, not give any structural information about the compound prepared on this particular batch of substrate. For this reason, the spatial arrangement of the substrate is irrelevant. Structural information will be accessible from the records of the sequences of reagents added to each batch of substrate. In every step of the preparation of a FCA or a NFCA, the exact location of one substrate-container within the array of containers and the structure of the different reagents added to this container is recorded, so that the precise structure of the thiazole resulting from one given container can always be deduced.

The resulting arrays of 2-methylenethiazoles may then be screened by comparing the individual thiazoles in terms of their ability to bind to a particular receptor or to induce a particular biological process or to catalyze a biological or chemical reaction. This can be achieved basically in two different ways. One possibility may be the screening of the substrate-bound thiazoles IIa, IIb, e.g. against a soluble receptor. This could for instance be a radioactively labelled peptide or enzyme, which would easily permit to determine the binding-strength of a given substrate-bound thiazole IIa, IIb to this peptide by washing away the excess of radioligand used and determining the remaining radioactivity of each substrate-bound thiazole IIa-, IIb-peptide complex. Alternatively, as a further example, catalytic activity of the different substrate-bound thiazoles IIa, IIb for a given biological process or a chemical reaction may be measured by comparing the speed at which this biological process or a chemical reaction takes place in the presence and in the absence of a given substrate-bound thiazole IIa, IIb.

The second option for screening may consist in screening the thiazoles Ia, Ib, after having cleaved the linker of the substrate-bound thiazoles IIa, IIb and using appropriately charged and indexed Microtiter plates of similar multiwell arrangements, in solution against an optionally substrate-bound receptor or enzyme. The screening of soluble small molecules is conventional and well known. Typically, radioassays are being used, in which the competitive binding of the radiolabelled, natural ligand of a given receptor and the compound to be tested for binding to this receptor is investigated.

An example would be a screening against the cholecystokinine receptors, which are widely distributed throughout the central and peripheral nervous system and mediate numerous physiological responses. Crude membrane homogenates may be prepared according to the procedure described by Chang et al. (*Proc. Natl. Acad. Sci.* 1986, 4923–4926) and radiolabelled cholecystokinine can be purchased from New England Nuclear, Mass., U.S.A. Other examples will be readily apparent to those skilled in the arts of physiology, biology and biotechnology. These could for instance be the somatostatine receptors, the glucagon receptors, the insulin receptor, the opiate receptors, the dopamine receptors, the acetylcholine receptors, the histamine receptors, etc.

Alternatively, functional or other assays may be used, in which for example the biological response of a cell or a genetically modified or unmodified organism is measured as a function of the amount of test-substance added to this organism. As a further example, the catalytic activity of the different thiazoles Ia, Ib for a given biological process or a chemical reaction may be measured by comparing the speed at which this biological process or a chemical reaction takes place in the presence and in the absence of a given thiazole Ia, Ib.

The methods described above may be used to prepare and screen large numbers of compounds in a reasonable amount of time. Synthesis may be combined with screening in various different ways to screen compounds in unusually large arrays.

References

1. Gallop, M. A.; Barrett, R. W.; Dower, W. J.; Fodor, S. P. A.; Gordon, E. M. *J. Med. Chem.* 1994, 37,1233–1251.
2. Gordon, E. M.; Barrett, R. W.; Dower, W. J.; Fodor, S. P. A.; Gallop, M. A. *J. Med. Chem.* 1994, 37,1385–1401.
3. Terreft, N. K.; Gardner, M.; Gordon, D. W.; Kobylecki, R. J.; Steele, J. *Tetrahedron.* 1995, 51, 8135–8173.
4. Lebl, M.; Krchnák, V.; Sepetov, N. F.; Kocis, P.; Patek, M.; Flegelova, Z.; Ferguson, R.; Lam, K. S. *Journal Of Protein Chemistry.* 1994, 13, 484–486.
5. Sepetov, N. F.; Krchnák, V.; Stankova, M.; Wade, S.; Lam, K. S.; Lebl, M. *Proc. Natl. Acad. Sci. USA* 1995, 92, 5426–5430.
6. Liskamp, R. M. J. *Angew. Chem. Int Ed. Engl* 1994, 33, 633–636.
7. Houghten, R. A.; Kay, B. K.; Madden, D.; Krchnák, V.; Lebl, M.; Chabala, J. C.; Kauffman, S. *Perspectives in Drug Discovery and Design* 1994, 2, 249–325.
8. Seligmann, B.; Abdul-Latif, F.; Al-Obeidi, F.; Flegelova, Z. *European Journal Of Medicinal Chemistry* 1995, 30, 319–335.
9. Baldwin, J. J.; Burbaum, J. J.; Henderson, I.; Ohimeyer, M. H. J. *J. Am. Chem. Soc.* 1995, 117, 5588–5589.
10. Jung et al., "Multiple Peptide Synthesis Methods and their Applications", *Angew. Chem. Int Ed. Engl.* 1992, 31, 367–383.
11. Laliberté, R.; Médawar, G. *Canadian Journal of Chemistry* 1970, 48, 2709–2717.
12. Gewald, K.; Hentschel, M. *Journal für Praktische Chemie* 1976, 318, 343–346.
13. Chiba, T.; Sato, H.; Kato, T. *Chemical And Pharmaceutical Bulletin.* 1982, 30, 3548–3554.
14. Gewald, K.; Hain, U.; Schmidt, M. *Journal für Praktische Chemie* 1986, 328, 459–464.
15. Augustin, M.; Dölling, W. *Journal für Praktische Chemie* 1982, 324, 322–328.
16. J. A. Eliman, Solid phase and combinatorial synthesis of benzodiazepine compounds on a solid support, U.S. Pat. No. 5,288,514; Feb. 22, 1994.
17. Sanfilippo, P. J., Jetter, M. C., Cordova, R., Noe, R. A., Chourmouzis, E., Lau, C. Y., and Wang, E. Novel thiazole based heterocycles as inhibitors of Ifa-1/icam-1 mediated cell-adhesion. *J. Med. Chem.* 1995, 38, 1057–1059.
18. Mohareb, R. M.; Aziz, S. I.; Abdel, S.; Nadia, I.; Shams, Hoda Zaki; *J. Chin. Chem. Soc.* (Taipei) 1992, 39, 181–187.
19. Mohareb, R. M.; Sherif, S. M.; *Arch. Pharm.* (Weinheim, Ger) 1991, 324 (1991), 469–471.
20. Mohareb, R. M.; Abdel-Sayed, N. I.; Sherif, S. M. *Phosphorus, Sulfur Silicon Relat. Elem.* 1991, 63,119–129.
21. Mohareb, R. M.; Sherif, S. M.; Abdel-Sayed, N. I.; Abdel-Aal, F. A. M.; *Liebigs Ann. Chem.* 1990, 11, 1143–1146.

EXAMPLES

Synthesis of 2-(3,4-diphenyl-3H-thiazol-2-ylidene)-3-oxo-3-piperazin-1-ylpropionitrile trifluoroacetate To a suspension of Wang resin (45.0 g, 42.3 mmol, Novabiochem, loading: 0.94 mmol/g) in DCM (600 mL) first pyridine (52 mL) and then a solution of 4-nitrophenyl chloroformed (43.0 g, 231 mmol) was added. After shaking for 3 h at room temperature the mixture was filtered, the resin was washed with DCM (5×300 mL) and then added to a cold solution of piperazine (38.2 g, 444 mmol) in DMF (600 mL). The resulting mixture was stirred for 13 h, filtered and the resin was washed extensively with DMF, DCM and methanol. After drying approx. 45 g of the carbamate-resin 1 was obtained.

To the DCM-swollen resin 1 (0.20 g, approx. 0.2 mmol) a solution of cyanoacetic acid (0.17 g, 2.02 mmol) in DMF (1.5 mL) and DCM (1.5 mL) was added, followed by the addition of diisopropylcarbodiimide (0.14 mL, 0.89 mmol). The resulting mixture was shaken for 3 h, filtered, washed with DMF (3×6 mL) and treated once more with cyanoacetic acid and diisopropylcarbodiimide as above for 3 h, to give, after washing with DMF, the resin bound cyanoacetamide 2.

A solution of DBU (0.7 mL) in DMF (2.5 mL) was added to the resin 2, followed by the addition of phenyl isothiocyanate (0.24 mL, 2.02 mmol). The mixture was shaken for 18 h, filtered, and the resin was extensively washed with DMF.

A solution of phenacyl chloride (0.32 g, 2.08 mmol) in DMF (2.5 mL) was then added to the resin, followed by the addition of glacial acetic acid (0.25 mL), and the mixture was shaken for 20 h.

After filtration the resin was carefully washed with DMF, methanol, DCM and 10% AcOH in DCM. It was then suspended in DCM (2 mL) and TFA (2 mL) and shaken for 3 h. Filtration, washing with DCM and concentration of the filtrates yielded 126 mg of 2-(3,4-diphenyl-3H-thiazol-2-ylidene)-3-oxo-3-piperazin-1-ylpropionitrile trifluoroacetate as an oil, which crystallized as hemihydrate upon addition of methanol and DCM.

Yellow solid, mp 233°–235° C.; HPLC (Lichrosorb RP 18, acetonitrile/water gradient, monitored at 254 nm): elution at 16.5 min, 88% pure. $^1$H NMR (400 MHz, DMSO-d$_6$)

δ 3.08 (s, br, 4H), 3.54 (s, br, 4H), 7.12–7.42 (m, 11H), 8.90 (s, br, 2H); $^{13}$C NMR (100 MHz, DMSO-d$_6$) δ 42.52 (t), 64.65 (s), 109.64 (d), 116.57 (s), 128.00 (d), 129.06 (d), 129.13 (d), 129.52 (d), 129.63 (s), 129.86 (d), 130.10 (d), 136.73 (s), 142.47 (s), 168.16 (s), 169.57 (s); IR (KBr): ν 3445, 3120, 2728, 2171 (CN), 1666, 1599 cm$^{-1}$; MS: 389 (MH$^+$). Anal. Calcd. for C$_{24}$H$_{21}$F$_3$N$_4$O$_3$S (502.51)+½ H$_2$O: C$_1$ 56.35; H, 4.33; N, 10.95. Found: C, 56.18; H, 4.26; N, 10.82.

Following this procedure, the following thiazole derivatives have been prepared:

2-(3,4-diphenyl-3H-thiazol-2-ylidene)-3-oxo-3-piperazin-1-ylpropionitrile trifluoroacetate

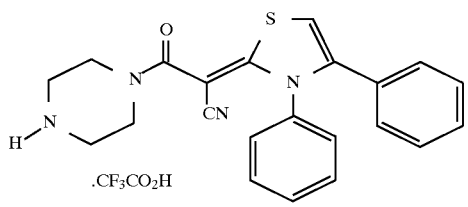

Yellow solid, mp 233°–235° C.; HPLC (Lichrosorb RP 18, acetonitrile/water gradient, monitored at 254 nm): elution at 16.5 min, 88% pure. $^1$H NMR (400 MHz, DMSO-d$_6$) δ 3.08 (s, br, 4H), 3.54 (s, br, 4H), 7.12–7.42 (m, 11H), 8.90 (s, br, 2H); $^{13}$C NMR (100 MHz, DMSO-d$_6$) δ 42.52 (t), 64.65 (s), 109.64 (d), 116.57 (s), 128.00 (d), 129.06 (d), 129.13 (d), 129.52 (d), 129.63 (s), 129.86 (d), 130.10 (d), 136.73 (s), 142.47 (s), 168.16 (s), 169.57 (s); IR (KBr): ν 3445, 3120, 2728, 2171 (CN), 1666, 1599 cm$^{-1}$; MS: 389 (MH$^+$). Anal. Calcd. for C$_{24}$H$_{21}$F$_3$N$_4$O$_3$S (502.51)+½ H$_2$O: C$_1$ 56.35; H, 4.33; N, 10.95. Found: C, 56.18; H, 4.26; N, 10.82.

2-[3-(4-dimethylaminophenyl)-4-phenyl-3H-thiazol-2-ylidene]-3-oxo-3-piperazin-1-yl-propionitrile trifluoroacetate

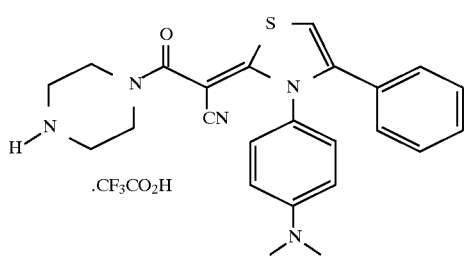

Yellow solid, mp >240° C.; HPLC (Lichrosorb RP 18, acetonitrile/water gradient, monitored at 254 nm): elution at 15.6 min, 69% pure. $^1$H NMR (400 MHz, DMSO-d$_6$) δ 2.89 (s, 6H), 3.08 (s, br, 4H), 3.55 (s, br, 4H), 6.59 (d, J=9.2 Hz, 2H), 7.12 (d, J=9.2 Hz, 2H), 7.16 (s, 1H), 7.17–7.20 (m, 2H), 7.22–7.31 (m, 3H), 8.82 (s, br, 2H); $^{13}$C NMR (100 MHz, DMSO-d$_6$) δ 40.67, 42.57, 42.67, 64.70, 109.26, 111.41, 115.31 (q, J=273 Hz), 116.77, 125.17, 128.00, 128.90, 129.73, 129.88, 129.96, 143.22, 150.50, 158.37 (q, J=37 Hz), 169.04, 169.83; IR (KBr): ν 3438, 3011, 2973, 2174 (CN), 1597, 1523 cm$^{-1}$; MS: 432 (MH$^+$), 346. Anal. Calcd. for C$_{24}$H$_{25}$N$_5$OS (431.55, free amine, mp 203°–205° C.)+1 H$_2$O: C, 64.12; H, 6.05; N, 15.58. Found: C, 63.79; H, 5.89; N, 15.16.

2-[4-(2,4-dichlorophenyl)-3-phenyl-3H-thiazol-2-ylidene]-3-oxo-3-piperazin-1-yl-propionitrile trifluoroacetate

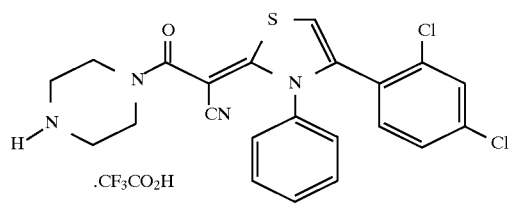

HPLC (Lichrosorb RP 18, acetonitrile/water gradient, monitored at 254 nm): elution at 19.9 min, 87% pure. $^1$H NMR (400 MHz, DMSO-d$_6$) δ 3.08 (s, br, 4H), 3.56 (s, br, 4H), 7.29–7.42 (m, 6H), 7.49 (dd, J=8.3, 1.5 Hz, 1H), 7.57 (t, J=1.5 Hz, 1H), 8.92 (s, br, 2H); $^{13}$C NMR (100 MHz, DMSO-d$_6$) δ 42.46 (t), 42.58 (t), 64.80 (s), 111.49 (d), 115.60 (q, J=273 Hz), 116.31 (s), 127.06 (d), 127.77 (s), 128.64 (d), 129.03 (d), 130.24 (d), 134.72 (d), 134.89 (s), 135.45 (s), 136.18 (s), 137.66 (s), 158.00 (q, J=37 Hz), 167.91 (s), 169.30 (s); IR (KBr): ν 3450, 3068, 2499, 2180 (CN), 1678, 1597, 1418 cm$^{-1}$; MS: 457, 459 (MH$^+$).

2-[4-(3,4-dihydroxyphenyl)-3-phenyl-3H-thiazol-2-ylidene]-3-oxo-3-piperazin-1-yl-propionitrile trifluoroacetate

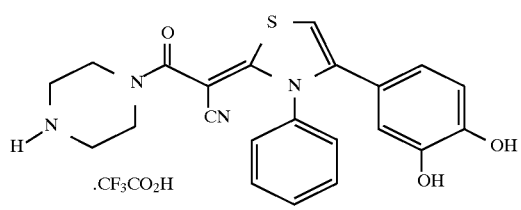

Yellow solid, mp >240° C.; HPLC (Lichrosorb RP 18, acetonitrile/water gradient, monitored at 254 nm): elution at 10.1 min, 81% pure. $^1$H NMR (400 MHz, DMSO-d$_6$) δ 3.08 (s, br, 4H), 3.56 (s, br, 4H), 6.36 (dd, J=9.0, 1.5 Hz, 1H), 6.53 (d, J=1.5 Hz, 1H), 6.54 (d, J=9.0 Hz), 7.15–7.50 (m, 5H), 9.20 (s, br, 2H); $^{13}$C NMR (100 MHz, DMSO-d$_6$) δ 42.49 (t), 64.46 (s), 108.24 (d), 114.91 (d), 115.60 (q, J=273 Hz), 117.29 (d), 118.51 (s), 120.25 (s), 121.23 (d), 129.02 (d), 129.40 (d), 129.90 (d), 136.93 (s), 143.06 (s), 144.66 (s), 146.19 (s), 158.55 (q, J=37 Hz), 167.95 (s), 169.64 (s); IR (KBr): ν 3647, 3111, 2859, 2175 (CN), 1675, 1573 cm$^{-1}$; MS: 421 (MH$^+$). Anal. Calcd. for C$_{22}$H$_{20}$N$_4$O$_3$S (420.49, free amine)+1.5 H$_2$O: C, 59.05; H, 5.18; N, 12.52. Found: C, 59.02; H, 4.75; N, 12.27.

2-(5-methyl-3,4-diphenyl-3H-thiazol-2-ylidene)-3-oxo-3-piperazin-1-yl-propionitrile trifluoroacetate

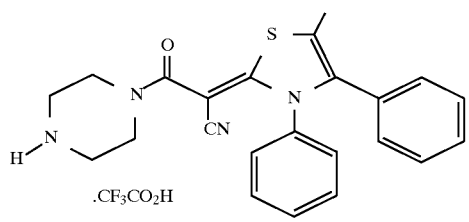

HPLC (Lichrosorb RP 18, acetonitrile/water gradient, monitored at 254 nm): elution at 18.0 min, 82% pure. $^1$H NMR (400 MHz, DMSO-$d_6$) δ 2.08 (s, 3H), 3.10 (s, br, 4H), 3.59 (s, br, 4H), 7.16 (m, 2H), 7.21–7.36 (m, 8H), 8.99 (s, br, 2H). $^{13}$C NMR (100 MHz, DMSO-$d_6$) δ 11.31 (q), 42.52 (t), 42.60 (t), 64.05 (s), 115.36 (q, J=273 Hz), 116.74 (s), 118.85 (s), 128.09 (d), 128.77 (s), 128.91 (d), 129.32 (d), 129.77 (d), 130.78 (d), 137.27 (s), 137.82 (s), 158.52 (q, J=37 Hz), 166.04 (s), 169.61 (s); MS: 402 (M$^+$).

2-(4-ethoxycarbonyl-4-hydroxy-
3-phenylthiazolidin-2-ylidene)-
3-oxo-3-piperazin-1-yl-
propionitrile trifluoroacetate

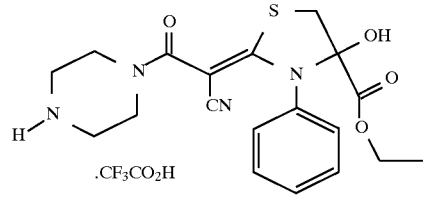

HPLC (Lichrosorb RP 18, acetonitrile/water gradient, monitored at 254 nm): elution at 8.1 min, 71% pure. $^1$H NMR (400 MHz, DMSO-$d_6$) δ 0.91–1.09 (m, 3H), 3.09 (s, br, 4H), 3.30 (d, J=12.0 Hz, 1H), 3.58 (s, br, 4H), 3.68 (d, J=12.0 Hz, 1H), 3.91–4.05 (m, 2H), 7.20–7.52 (m, 5H), 8.99 (s, br, 2H); $^{13}$C NMR (100 MHz, DMSO-$d_6$) δ 13.41 (q), 40.00 (t), 42.49 (t), 62.28 (t), 69.74 (s), 96.54 (s), 115.15 (s), 115.52 (q, J=273 Hz), 128.58 (d), 128.85 (d), 128.89 (d), 137.24 (s), 158.47 (q, J=37 Hz), 166.82 (s), 167.71 (s), 170.76 (s); IR (KBr): ν 3477, 2189 (CN), 1679, 1423 cm$^{-1}$; MS: 385 (MH$^+$), 299.

2-(ethyl-5-methyl-4-phenyl-3H-thiazol-
2-ylidene)-3-oxo-3-piperazin-1-yl-
propionitrile trifluoroacetate

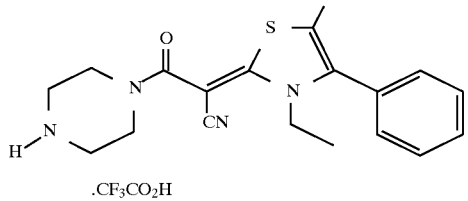

HPLC (Lichrosorb RP 18, acetonitrile/water gradient, monitored at 254 nm): elution at 17.3 min, 86% pure. $^1$H NMR (400 MHz, DMSO-$d_6$) δ 1.12 (t, J=7.4 Hz, 3H), 1.99 (s, 3H), 3.17 (s, br, 4H), 3.72 (s, br, 4H), 4.13 (q, J=7.4Hz, 2H), 7.43 (m, 2H), 7.58 (s, 3H), 9.07 (s, br, 2H). $^{13}$C NMR (100 MHz, DMSO-$d_6$) δ 11.21 (q), 13.75 (q), 42.65 (t), 42.69 (t), 43.78 (t), 61.37 (s), 115.43 (q, J=273 Hz), 119.89 (s), 120.20 (s), 128.99 (s), 129.04 (d), 129.80 (d), 130.60 (d), 137.86 (s), 158.48 (q, J=37 Hz), 164.71 (s), 169.69 (s); IR (KBr): ν 3468, 2173 (CN), 1680, 1599 cm$^{-1}$; MS: 354 (M$^+$), 269.

2-[4-(3,4-dihydroxyphenyl)-
3-ethyl-3H-thiazol-2-ylidene]-
3-oxo-3-piperazin-1-yl-
propionitrile trifluoroacetate

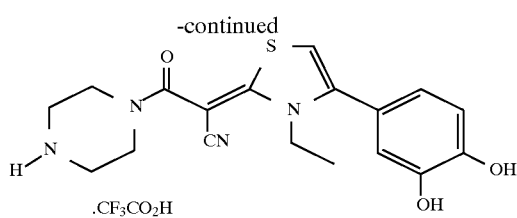

Yellow solid, mp 223°–225° C.; HPLC (Lichrosorb RP 18, acetonitrile/water gradient, monitored at 254 nm): elution at 8.4 min, 91% pure. $^1$H NMR (400 MHz, DMSO-$d_6$) δ 1.12 (t, J=7.4 Hz, 3H), 3.15 (s, br, 4H), 3.70 (s, br, 4H), 4.26 (q, J=7.4 Hz, 2H), 6.71 (dd, J=8.5, 1.5 Hz, 1H), 6.80 (d, J=1.5 Hz, 1H), 6.86 (d, J=8.5 Hz, 1H), 6.99 (s, 1H), 9.00 (s, br, 2H). $^{13}$C NMR (100 MHz, DMSO-$d_6$) δ 14.14 (q), 42.95 (t), 43.01 (t), 43.61 (t), 62.34 (s), 110.04 (d), 116.00 (d), 116.30 (q, J=273 Hz), 117.29 (d), 120.07 (s), 120.65 (s), 121.51 (d), 143.61 (s), 145.68 (s), 149.27 (s), 158.48 (q, J=37 Hz), 166.91 (s), 169.96 (s); IR (KBr): ν 3357, 3113, 3000, 2496, 2181 (CN), 1738, 1671, 1611 cm$^{-1}$. Anal. Calcd. for $C_{20}H_{21}F_3N_4O_5S$ (486.46)+1.5 $H_2O$: C, 46.78; H, 4.71. Found: C, 47.28; H, 4.51.

2-(4-hydroxy-3-phenyl-4-trifluoromethyl-
thiazolidin-2-ylidene)-3-oxo-3-piperazin-
1-ylpropionitrile trifluoroacetate

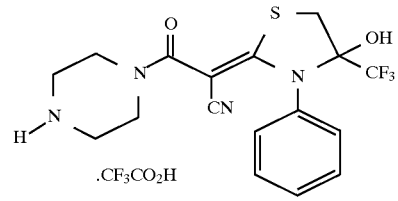

HPLC (Lichrosorb RP 18, acetonitrile/water gradient, monitored at 254 nm): elution at 12.8 min, 87% pure. $^1$H NMR (400 MHz, DMSO-$d_6$) δ 3.08 (s, br, 4H), 3.47 (d, J=12.9 Hz, 1H), 3.54 (s, br, 4H), 3.73 (d, J=12.9 Hz, 1H), 7.25–7.48 (m, 5H), 8.89 (s, br, 2H); IR (KBr): ν 3066, 2196 (CN), 1674, 1434 cm$^{-1}$; MS: 399 (MH$^+$).

CONCLUSION

The above description is illustrative and not restrictive. Various modifications and variations of the invention will become apparent to those of skill in the art upon review of this disclosure. Merely by way of example a wide variety of process times, reaction temperature as well as different ordering of certain processing steps may be utilized. The scope of the invention should, therefore, be determined, not with reference to the above description, but instead should be determined with reference to the appended claims along with their full scope of equivalents.

I claim:
1. A compound of the general formula Ia or Ib

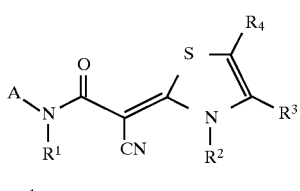

and

-continued

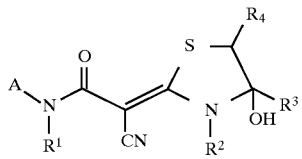

wherein

A is a group of formula

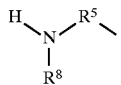

or

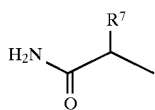

wherein $R^5$ is alkylene optionally substituted with hydrogen, alkyl, aryl, heteroaryl, alkoxy, aryloxy, cyano, hydroxy, dialkylamino, arylalkylamino, diarylamino or halogen;

$R^6$ is hydrogen, alkyl optionally substituted with hydroxy, halogen, cyano, alkoxy, aryloxy, dialkylamino, arylalkylamino or diarylamino; or aralkyl;

$R^5$ and $R^6$ may be covalently linked to each other by a covalent bond or an additional alkylene group $R^5$, thereby giving rise to a fragment of the type shown below

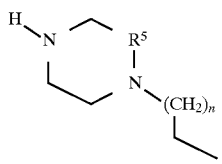

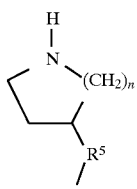

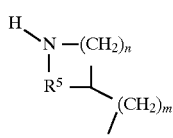

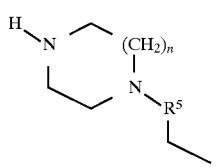

-continued

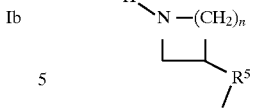
Ib wherein n and m are integers between 0 and 15;

$R^7$ is hydrogen, alkyl, alkyl substituted with hydroxy, alkoxy, aryloxy, alkylthio, arylthio, dialkylamino, arylalkylamino or diarylamino; aralkyl, aryl, aryl substituted with alkyl, aryl, heteroaryl, halogen, alkoxy, aryloxy, dialkylamino, alkylarylamino, diarylamino, halogen, cyano, alkoxycarbonyl or aminocarbonyl;

$R^1$ is hydrogen, alkyl optionally substituted with hydroxy, halogen, cyano, alkoxy, aryloxy, dialkylamino, arylalkylamino or diarylamino; or aralkyl;

$R^1$ may be covalently linked to A, $R^5$, $R^6$ and/or $R^7$, in which case —$R^1$—A— or —$R^1$—$R^5$— represents low alkylene, unsubstituted or substituted with alkyl, hydroxy, alkoxycarbonyl, alkoxy or dialkylamino, —$R^1$—$R^6$— represents ethylene or propylene, unsubstituted or substituted with alkyl, hydroxy, alkoxy or dialkylamino, and/or —$R^1$—$R^7$— represents methylene, propylene or butylene unsubstituted or substituted with alkyl, hydroxy, alkoxycarbonyl, alkoxy or dialkylamino;

$R^2$ is alkyl optionally substituted with aryl, heteroaryl, alkoxy, aryloxy, cyano, dialkylamino, arylalkylamino, diarylamino or halogen;

aryl optionally substituted with alkyl, aryl, heteroaryl, halogen, alkoxy, aryloxy, dialkylamino, alkylarylamino, diarylamino, halogen, cyano, alkoxycarbonyl or aminocarbonyl; heteroaryl optionally substituted with alkyl, aryl, heteroaryl, halogen, alkoxy, aryloxy, dialkylamino, alkylarylamino, diarylamino, halogen, cyano, alkoxycarbonyl or aminocarbonyl; and $R^3$ is cyano, alkyl optionally substituted with alkoxycarbonyl or halogen, aryl optionally substituted with alkyl, aryl, heteroaryl, halogen, alkoxy, aryloxy, dialkylamino, alkylarylamino, diarylamino, halogen, cyano, alkoxycarbonyl or aminocarbonyl, heteroaryl or alkoxycarbonyl;

$R^4$ is hydrogen or substituted or unsubstituted alkyl, acyl, aminocarbonyl or aryl; and pharmaceutically acceptable salts thereof.

2. The compound according to claim 1, wherein the compounds of formula Ia, Ib are selected from the group consisting of:

2-(3,4-diphenyl-3H-thiazol-2-ylidene)-3-oxo-3-piperazin-1-ylpropionitrile;

2-[3-(4-dimethylaminophenyl)-4-phenyl-3H-thiazol-2-ylidene]-3-oxo-3-piperazin-1-ylpropionitrile;

2-[4-(2,4-dichlorophenyl)-3-phenyl-3H-thiazol-2-ylidene]-3-oxo-3-piperazin-1-ylpropionitrile;

2-[4-(3, 4-dihydroxyphenyl)-3-phenyl-3H-thiazol-2-ylidene]-3-oxo-3-piperazin-1-ylpropionitrile;

2-(5-methyl-3,4-diphenyl-3H-thiazol-2-ylidene)-3-oxo-3-piperazin-1-ylpropionitrile;

2-(4-ethoxycarbonyl-4-hydroxy-3-phenylthiazolidine-2-ylidene)-3-oxo-3-piperazin- 1-ylpropionitrile;

2-(3-ethyl-5-methyl-4-phenyl-3H-thiazol-2-ylidene)-3-oxo-3-piperazin-1-ylpropionitrile;

2-[4-(3,4-dihydroxyphenyl)-3-ethyl-3H-thiazol-2-ylidene]-3-oxo-3-piperazin-1-ylpropionitrile; and 2-(4-hydroxy-3-phenyl-4-trifluoromethylthiazolidin-2-ylidene]-3-oxo-3-piperazin-1-ylpropionitrile;

or pharmaceutically acceptable salts thereof.

* * * * *